United States Patent
Commo

(10) Patent No.: US 8,895,037 B2
(45) Date of Patent: Nov. 25, 2014

(54) ADMINISTATION OF ELLAGIC ACID FOR THE TREATMENT OF CANITIES

(75) Inventor: Stephane Commo, Chaville (FR)

(73) Assignee: L'Oreal, Paris (FR)

(*) Notice: Subject to any disclaimer, the term of this patent is extended or adjusted under 35 U.S.C. 154(b) by 412 days.

(21) Appl. No.: 11/812,572

(22) Filed: Jun. 20, 2007

(65) Prior Publication Data

US 2008/0026019 A1 Jan. 31, 2008

Related U.S. Application Data

(60) Provisional application No. 60/819,398, filed on Jul. 10, 2006.

(30) Foreign Application Priority Data

Jun. 20, 2006 (FR) .................................. 06 52552

(51) Int. Cl.
- *A61K 8/02* (2006.01)
- *A61Q 5/06* (2006.01)
- *A61K 8/49* (2006.01)

(52) U.S. Cl.
CPC .............. *A61K 8/498* (2013.01); *A61Q 5/065* (2013.01)
USPC ........................................................ 424/401

(58) Field of Classification Search
None
See application file for complete search history.

(56) References Cited

U.S. PATENT DOCUMENTS

| | | | |
|---|---|---|---|
| 5,002,785 A * | 3/1991 | Lew | 426/303 |
| 5,073,545 A * | 12/1991 | Arima et al. | 514/27 |
| 5,843,987 A * | 12/1998 | Rajagopalan et al. | 514/453 |
| 6,037,326 A * | 3/2000 | Styczynski et al. | 514/23 |
| 6,187,325 B1 | 2/2001 | Pelletier et al. | |
| 6,403,086 B1 * | 6/2002 | Yegorova | 424/94.2 |
| 7,037,539 B2 * | 5/2006 | Westphal et al. | 426/51 |
| 2002/0076444 A1 * | 6/2002 | Di Costanzo et al. | 424/489 |
| 2002/0098213 A1 * | 7/2002 | Bonte et al. | 424/401 |
| 2002/0127256 A1 * | 9/2002 | Murad | 424/401 |
| 2004/0014700 A1 * | 1/2004 | Kurfurst et al. | 514/44 |
| 2004/0131656 A1 * | 7/2004 | Roufs et al. | 424/439 |
| 2006/0251753 A1 * | 11/2006 | Alkayali | 424/776 |

FOREIGN PATENT DOCUMENTS

| | | |
|---|---|---|
| EP | 1437119 A1 | 7/2004 |
| FR | 2782920 A1 | 3/2000 |
| JP | 01079103 | 3/1989 |
| JP | 11/124318 | 5/1999 |
| JP | 11/322569 | 11/1999 |
| JP | 2001/517688 | 10/2001 |

(Continued)

OTHER PUBLICATIONS

Broomfield, Healthopedia.com (Jul. 27, 2001).*

(Continued)

*Primary Examiner* — Trevor Love
(74) *Attorney, Agent, or Firm* — Buchanan Ingersoll & Rooney PC

(57) ABSTRACT

At least one compound selected from among ellagic acid, its salts, its metal complexes, its monoether or polyether, monoacylated or polyacylated derivatives and its carbonate or carbamate derivatives deriving from hydroxyl groups and mixtures thereof, and admixtures thereof with other active agents selected from among active agents for combating desquamative conditions of the scalp, plant extracts having propigmenting activity and active agents that slow hair loss and/or promote hair regrowth, are useful for preventing and/or limiting and/or stopping the development of canities.

10 Claims, 2 Drawing Sheets

(56) References Cited

FOREIGN PATENT DOCUMENTS

| JP | 2002/020242 | 1/2002 |
|---|---|---|
| JP | 2004/352628 | 12/2004 |
| WO | WO 99/16415 A1 | 4/1999 |

OTHER PUBLICATIONS

Bolduc et al. (Clinics in Dermatology, 2001; 19:431-436.*
Iwasaki et al., Derwent Abstract HP 2003/246716. Pub. Sep. 2, 2003.*
Prevent definition. Wordnet.com.*
Adams, Can Hair Loss Be Reversed Through Nutrition? Greendivamom.com, pub. Oct. 13, 2004.*
Hakkinen et al. Ellagic acid content in berries: Influence of doestic processing and storage, Eu Food Res Technol, 2000, 212: 75-80.*
No Truth to the Fountain of Youth, Jun. 2002.*
Kids Health. Skin, Hair and Nails. Published 2011.*
Neste et al. Hair cycle and hair pigmentation: dynamic interactions and changes associated with aging. Micron 35 (2004) 193-200.*
Meyer, Laurence, Why does hair turn gray?, Mar. 26, 2001, Scientific American, http://www.scientificamerican.com/article.cfm?id=why-does-hair-turn-gray, last accessed Oct. 27, 2011.*
Eure, Marian, Gastroesophageal Reflux Update, 2005, About.com, p. 1, http://seniorhealth.about.com/cs/digestivetract/a/GERD.htm?p=1.*
XP 002416789, JP 2001 302543; Database WPI Week 200215, 2002-110023, Oct. 21, 2001, Derwent Publications Ltd., London, GB.
XP 002416790, JP 2002 012519; Database WPI Week 200231, 2002-263145, Jan. 15, 2002, Derwent Publications Ltd., London, GB.
XP 002417058, JP 2005 082527; Database WPI Week 200529, 2005-276277, Mar. 31, 2005, Derwent Publications Ltd., London, GB.
French Search Report corresponding to FR 0652552 issued on Jan. 30, 2007—1 page.
*Diseases of the Hair and Scalp*, edited by Rodney Dawber, 3rd edition (1997): Chapter 12:"The Colour of the Hair" Dawber and Gummer, p. 397-410, Blackwell Science.
Petra Clara Arck et al., "Towards a 'Free Radical Theory of Graying': Melanocyte Apoptosis in the Aging Human Hair Follicle is an Indicator of Oxidative Stress Induced Tissue Damage" *The FASEB Journal •FJ Express Summary* vol. 20 (Jul. 2006) p. 1567-1569.
*The Science of Hair Care*, edited by Claude Bouillon, 2d edition (2005): Chapter 19: "Alopecia", Reygagne and de Lacharriere, p. 559-582, CRC Press.
"The Age-Prevalence of Arcus Senilis, Greying of Hair, and Baldness. Etiological Considerations" Philip R.J. Burch et al, *Journal of Gerontology* (1971) vol. 26, No. 3, p. 364-372.
S. Commo et al., *Cutaneous Biology* "Human Hair Greying is Linked to a Specific Depletion of Hair Follicle Melanocytes Affecting Both the Bulb and the Outer Root Sheath" *British Journal of Dermatology* (2004) vol. 150, p. 435-443.
Navindra P. Seeram "Berry Fruits for Cancer Prevention: Current Status and Future Prospects" *J. Agric. Food Chem* (2008) vol. 56, p. 630-635, American Chemical Society.
Yanjun Zhang et al., "Isolation and Identification of Strawberry Phenolics with Antioxidant and Human Cancer Cell Antiproliferative Properties" *J. Agric. Food Chem.* (2008) vol. 56 p. 670-675, American Chemical Society.
English translation of the Japanese Office Action mailed on Jul. 17, 2012, in corresponding Japanese Patent Application 2007-161727.
Nippon Nogeikagaku Kaishi, vol. 62, 166-169 (1988).
D.A. Vattem et al., *Biological Functionality of Ellagic Acid: A Review*, 29 J. Food. Biochem. 234-266 (2005).

* cited by examiner

ADMINISTATION OF ELLAGIC ACID FOR THE TREATMENT OF CANITIES

CROSS-REFERENCE TO PRIORITY/PROVISIONAL APPLICATIONS

This application claims priority under 35 U.S.C. §119 of FR 06/52552, filed Jun. 20, 2006, and of U.S. Provisional application Ser. No. 60/819,398, Jul. 10, 2006, each hereby expressly incorporated by reference and each assigned to the assignee hereof.

BACKGROUND OF THE INVENTION

1. Technical Field of the Invention

The present invention relates to the cosmetic administration of ellagic acid, its salts, its metal complexes, its monoether or polyether, monoacylated or polyacylated derivatives and its carbonate or carbamate derivatives deriving from hydroxyl groups for treating canities.

2. Description of Background and/or Related and/or Prior Art

The hair follicle is a tubular invagination of the epidermis which extends to the deep layers of the dermis. The lower part, or hair bulb, itself comprises an invagination in which the dermal papilla is located. The lower part of the bulb is an area of cell proliferation where the precursors of keratinized cells that make up hair are found. The ascending cells derived from these precursors become gradually keratinized in the upper part of the bulb, and this assembly of keratinized cells will form the hair shaft.

The color of head hair and of body hair depends, in particular, on the presence, in variable amounts and ratios, of two groups of melanins: eumelanins (brown and black pigments) and pheomelanins (red and yellow pigments). The pigmentation of head hair and body hair requires the presence of melanocytes in the bulb of the hair follicle. These melanocytes are in an active state, that is to say that they synthesize melanins. These pigments are transmitted to the keratinocytes intended to form the hair shaft, which will result in the growth of a pigmented head hair or body hair. This structure is hereinafter called "follicular pigmentation unit".

In mammals, melanogenesis involves at least three enzymes: tyrosinase, DOPAchrome tautomerase (TRP-2, for Tyrosinase Related Protein 2) and DHICA oxidase (TRP-1, for Tyrosinase Related Protein 1).

Tyrosinase is the enzyme that initiates the biosynthesis of melanins. It is also described as being the limiting enzyme of melanogenesis.

TRP-2 catalyzes the tautomerization of DOPAchrome to 5,6-dihydroxyindole-2-carboxylic acid (DHICA). In the absence of TRP-2, DOPAchrome undergoes a spontaneous decarboxylation to form 5,6-dihydroxyindole (DHI).

DHICA and DHI are both pigment precursors, TRP-1 oxidizes the DHICA molecules to form quinone derivatives (Pawelek, J. M. and Chakraborty, A. K., "The Enzymology of Melanogenesis", In: "The Pigmentary System: Physiology and Pathophysiology", by Nordlund, J. J., Boissy, R. E., Hearing, V. J., King, R. A., and Ortonne, J-P., New York, Oxford University Press, 1998, p. 391-400).

The three enzymes, tyrosinase, TRP-2 and TRP-1, appear to be specifically involved in melanogenesis. In addition, the activity of these three enzymes has been described as being necessary to the maximum activity of biosynthesis of eumelanins.

Head hair and body hair undergo a cycle. This cycle comprises a growth phase (anagen phase), a degenerative phase (catagen phase) and a rest phase (telogen phase) following which a new anagen phase will develop. Due to this hair cycle, and unlike the epidermal pigmentation unit, the follicular pigmentation unit must also be cyclically renewed.

Canities (natural hair whitening) is linked to a specific and gradual depletion of the hair melanocytes which affects both the melanocytes of the hair bulb and the precursor cells for melanocytes (Commo, et al., Br. J. Dermatol., 2004, 150, 435-443). Other cell types present in the hair follicles are not affected. In addition, this depletion of melanocytes is not observed in the epidermis. The cause of this gradual and specific depletion of melanocytes and melanocyte precursors in the hair follicle has not been identified to date.

It therefore appears necessary to combat the disappearance of melanocytes from human hair follicles, a process which affects both the active melanocytes of the bulbs and the quiescent melanocytes of the upper region of the hair follicles, in order to combat canities.

The assignee hereof has identified a means of combating hair whitening by acting on the TRP-2 enzyme (WO 03/103568) especially by increasing the level of GSH. Indeed, it has been demonstrated that the expression of the TRP-2 enzyme is correlated with a higher level of GSH in the melanocytes, the expression of TRP-2 induces an increase of the level of GSH in the melanocytes. Thus, in the melanocytes which do not express TRP-2 (for example, the melanocyte precursors of hair), there is a low level of GSH in comparison with melanocytes that express the TRP-2 enzyme (for example, all the skin melanocytes).

The assignee hereof has therefore identified a novel target for the treatment of canities, more particularly, it has been demonstrated that the compounds capable of increasing the GSH level in the melanocytes that are deficient in TRP-2 increase the viability of these melanocytes, decrease hair whitening and lead, unlike their depigmenting effect described in the literature, to the restoring of hair pigmentation (FR 04/13756).

SUMMARY OF THE INVENTION

It has now been demonstrated that ellagic acid, through its ability to increase the level of GSH (Khanduja, K. L., Food and Chemical Tox., 1999, 37, 313) in the melanocytes, counteracts hair whitening, unlike its skin depigmenting effect described in the literature, and effects the restoring of hair pigmentation.

Numerous prior patents describe the use of ellagic acid for its depigmenting, ultraviolet radiation screening, anti-cancer and anti-inflammatory properties (JP 2003/267818, EP-1, 021,161, EP-1,282,395).

The present invention features the administration of ellagic acid, its salts, its metal complexes, its monoether or polyether, monoacylated or polyacylated derivatives and its carbonate or carbamate derivatives deriving from hydroxyl groups as an agent that prevents, limits or stops the progression of canities, and maintains and/or promotes the natural repigmentation of head hair and/or body hair.

In particular, the present invention features the administration of ellagic acid, its salts, its metal complexes, its monoether or polyether, monoacylated or polyacylated derivatives and its carbonate or carbamate derivatives deriving from hydroxyl groups to prevent and/or limit and/or stop the development of canities.

This invention also features the administration of ellagic acid, its salts, its metal complexes, its monoether or polyether, monoacylated or polyacylated derivatives and its carbonate or carbamate derivatives deriving from hydroxyl groups for maintaining the natural pigmentation of grey head hair and/or body hair.

Ellagic acid, also known as 2,3,7,8-tetrahydroxy(1)benzopyrano(5,4,3-CDE)(1)benzopyran-5,10-dione, is a well known molecule belonging to the group of polyphenols and present in the plant kingdom. Reference may be made to the publication of the Merck Index, 20$^{th}$ Edition, (1996), No. 3588. A method of purifying ellagic acid and also purified ellagic acids obtained by such a method are described in FR-A-1,478,523.

Ellagic acid has the following chemical formula:

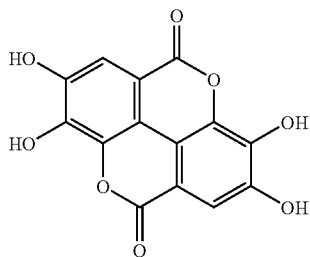 [SMILES: O=c1oc2c(O)c(O)cc3c(=O)oc4c(O)c(O)cc1c4c23]

which comprises four fused rings.

Ellagic acid is commercially available, especially from Sigma France.

Within the scope of the invention, the salts of ellagic acid comprise, in particular, the metal salts, especially alkali metal or alkaline-earth metal salts, such as the sodium and calcium salts, amine salts such as the salts of methylglutamine, diethanolamine, triethanolamine, choline or bis(triethylamine), salts of amino acids, especially salts of basic amino acids such as arginine, lysine and ornithine, metal complexes comprising, in particular, metal complexes with zinc and copper and monoacylated or polyacylated derivatives comprising, in particular, saturated or unsaturated acyl groups having from 2 to 22 carbon atoms. Preferably, these acyl groups correspond to acetic acid, palmitic acid, oleic acid, linoleic acid, linolenic acid, arachidonic acid, stearic acid, brassidic acid, erucic acid, behenic acid and (all Z)-5,8,11,14,17-eicosapentaenoic acid. The aforementioned monoether or polyether derivatives are, in particular, alkoxy derivatives having from 1 to 4 carbon atoms, or else condensation derivatives of one or more hydroxyl groups of ellagic acid with a sugar or a chain of sugars. In particular, it is 3-methoxyellagic acid or monoether or polyether derivatives with sugars such as glucose, arabinose, rhamnose and galactose.

The aforementioned ether or acylated derivatives may be obtained by polyphenol etherification or acylation methods well known to one skilled in this art. Some may also be obtained by extraction from plants.

The present invention also features compositions for combating canities, comprising, formulated into a cosmetically acceptable medium, at least one compound selected from ellagic acid, its salts, its metal complexes, its monoether or polyether, monoacylated or polyacylated derivatives and its carbonate or carbamate derivatives deriving from hydroxyl groups combined with one other hair active agent selected from agents for combating the desquamative conditions of the scalp and/or plant extracts with propigmenting activity.

This invention also features compositions for combating canities comprising, formulated into a cosmetically acceptable medium, at least one compound selected from ellagic acid, its salts, its metal complexes, its monoether or polyether, monoacylated or polyacylated derivatives and its carbonate or carbamate derivatives deriving from hydroxyl groups, combined with at least one agent that slows down hair loss or that promotes its regrowth.

Figure 1:
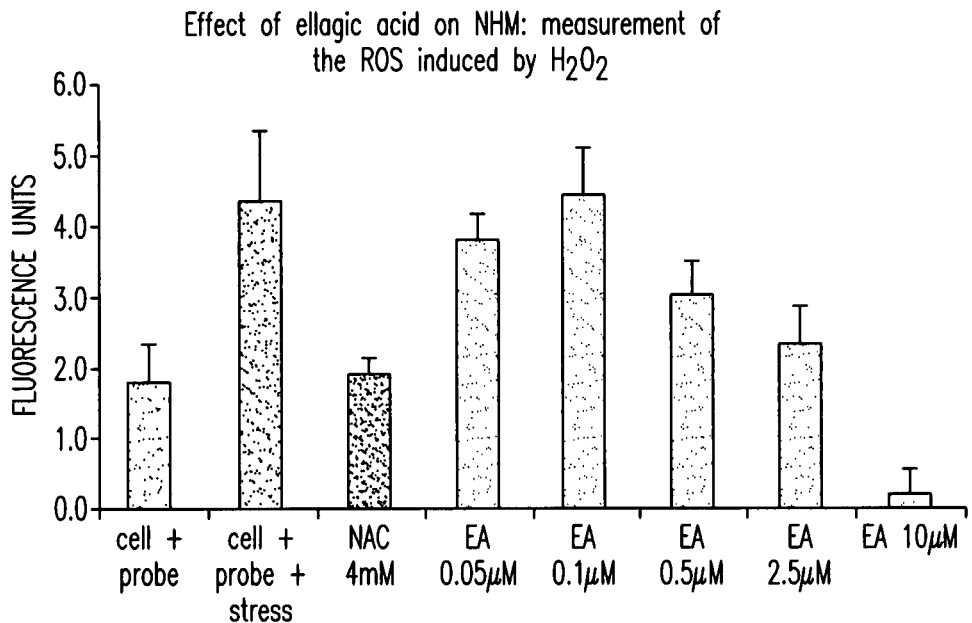
FIG. 1 is a graph showing the effect of ellagic acid on NHM: measurement of the ROS induced by $H_2O_2$.

DETAILED DESCRIPTION OF BEST MODE AND SPECIFIC/PREFERRED EMBODIMENTS OF THE INVENTION

The compositions according to the invention comprise an amount of a compound selected from ellagic acid, its salts, its metal complexes, its monoether or polyether, monoacylated or polyacylated derivatives and its carbonate or carbamate derivatives deriving from hydroxyl groups of from 0.001% to 10% by weight relative to the total weight of the composition, preferentially from 0.01% to 5% by weight relative to the total weight of the composition and even more preferentially from 0.1% to 1% by weight relative to the total weight of the composition.

The compositions according to the invention may be administered orally or applied topically to the skin (over any cutaneous area of the body covered with hair) and/or the scalp.

Orally, the compositions according to the invention may contain the compound or compounds selected from ellagic acid, its salts, its metal complexes, its monoether or polyether, monoacylated or polyacylated derivatives and its carbonate or carbamate derivatives deriving from hydroxyl groups in solution in a dietary liquid such as an optionally flavored aqueous or aqueous-alcoholic solution. They may also be incorporated into an ingestible solid excipient and may be, for example, in the form of granules, pills, tablets or sugar-coated tablets. They may also be dissolved in a dietary liquid that is itself optionally packaged in ingestible capsules.

Depending on the method of administration, whether regime or regimen, the compositions of the invention may be in any galenic form normally used, particularly in cosmetology.

A preferred composition of the invention is a cosmetic composition suitable for topical application to the scalp and/or the skin.

For a topical application, the composition that can be administered according to the invention may especially be in the form of an aqueous, aqueous-alcoholic or oily solution or of a dispersion of the lotion or serum type, of emulsions having liquid or semi-liquid consistency of the milk type, obtained by dispersion of a fatty phase in an aqueous phase (O/W) or conversely (W/O), or of suspensions or emulsions having a soft consistency of the aqueous or anhydrous gel or cream type, or else of microcapsules or microparticles, or of vesicular dispersions of ionic and/or non-ionic type. It may thus be in the form of an ointment, dye, cream, pomade, powder, patch, impregnated pad, solution, emulsion or vesicular dispersion, lotion, gel, spray, suspension, shampoo, aerosol or foam. They may be anhydrous or aqueous. It may also consist of solid preparations that form soaps or cleansing bars.

These compositions are formulated according to the usual methods.

The composition that is administered according to the invention may, in particular, be a composition for hair care, and especially a shampoo, a setting lotion, a treating lotion, a styling cream or gel, a dye composition (especially an oxidation dye composition) optionally in the form of coloring shampoos, restructuring lotions for the hair, or a mask.

The cosmetic composition according to the invention will preferentially be a cream, hair lotion, shampoo or conditioner.

The amounts of the various constituents of the compositions that are administered according to the invention are those conventionally used in the fields in question.

When the composition according to the invention is an emulsion, the amount of the fatty phase may range from 5% to 80% by weight, and preferably from 5% to 50% by weight, relative to the total weight of the composition. The oils, waxes, emulsifiers and coemulsifiers included in the composition in the form of an emulsion are selected from those conventionally used in the cosmetics field. The emulsifier and coemulsifier are present in the composition in an amount ranging from 0.3% to 30% by weight, and preferably from 0.5% to 20% by weight relative to the total weight of the composition. The emulsion may, in addition, contain lipid vesicles.

When the composition according to the invention is an oily solution or gel, the fatty phase may represent more than 90% of the total weight of the composition.

In one embodiment of the invention, the composition will be such that ellagic acid, its salts, its metal complexes, its monoether or polyether, monoacylated or polyacylated derivatives and its carbonate or carbamate derivatives deriving from hydroxyl groups is encapsulated in a coating such as microspheres, nanospheres, oleosomes or nanocapsules.

This type of formulation proves advantageous as it makes it possible to specifically target the hair follicle and thus to release the active agent on its site of action.

By way of example, the microspheres can be prepared according to the method described in EP-0,375,520.

The nanospheres can be in the form of an aqueous suspension and be prepared according to the methods described in FR-0015686 and FR-0101438.

Oleosomes consist of an oil-in-water emulsion formed by oily globules provided with a lamellar liquid crystal coating dispersed in an aqueous phase (see EP-0,641,557 and EP-0,705,593).

Ellagic acid, its salts, its metal complexes, its monoether or polyether, monoacylated or polyacylated derivatives or its carbonate or carbamate derivatives deriving from hydroxyl groups can also be encapsulated in nanocapsules consisting of a lamellar coating obtained from a silicon surfactant (see EP-0,780,115), the nanocapsules can also be prepared based on water-dispersible sulfonic polyesters (see FR-0113337).

Ellagic acid, its salts, its metal complexes, its monoether or polyether, monoacylated or polyacylated derivatives or its carbonate or carbamate derivatives deriving from hydroxyl groups could also be complexed to the surface of cationic oily globules, regardless of their size (see EP-1,010,413, EP-1,010,414, EP-1,010,415, EP-1,010,416, EP-1,013,338, EP-1,016,453, EP-1,018,363, EP-1,020,219, EP-1,025,898, EP-1,120,101, EP-1,120,102, EP-1,129,684, EP-1,160,005 and EP-1,172,077).

Ellagic acid, its salts, its metal complexes, its monoether or polyether, monoacylated or polyacylated derivatives or its carbonate or carbamate derivatives deriving from hydroxyl groups may finally be complexed to the surface of nanocapsules or nanoparticles provided with a lamellar coating (see EP-0,447,318 and EP-0,557,489) and containing a cationic surfactant at the surface (see the references cited previously for the cationic surfactants).

In particular, a composition will be preferred such that the coating containing ellagic acid, its salts, its metal complexes, its monoether or polyether, monoacylated or polyacylated derivatives or its carbonate or carbamate derivatives deriving from hydroxyl groups has a diameter of less than or equal to 10 μm. When the coating does not form a spherical vesicle, the diameter is understood to be the largest dimension of the vesicle.

In a known manner, the compositions according to the invention may also contain adjuvants that are customary in the cosmetics field, such as hydrophilic or lipophilic gelling agents, hydrophilic or lipophilic additives, preservatives, antioxidants, solvents, fragrances, fillers, screening agents, odor absorbers and coloring materials. The amounts of these various adjuvants are those conventionally used in the cosmetics field, and are, for example, from 0.01% to 10% of the total weight of the composition. These adjuvants, depending on their type, may be introduced into the fatty phase, into the aqueous phase and/or into the lipid spherules.

The compositions according to the invention may combine at least one compound selected from ellagic acid, its salts, its metal complexes, its monoether or polyether, monoacylated or polyacylated derivatives and its carbonate or carbamate derivatives deriving from hydroxyl groups with other active agents. Among these active agents, exemplary are:

agents modulating the differentiation and/or proliferation and/or pigmentation of skin cells such as retinol and esters thereof, vitamin D and derivatives thereof, oestrogens such as oestradiol, cAMP modulators such as POMC derivatives, adenosine, or forskolin and derivatives thereof, prostaglandins and derivatives thereof, triiodotrionine and derivatives thereof;

plant extracts such as those from *Iridaceae* or from soybean, which extracts may or may not then contain isoflavones;

extracts of microorganisms;

free-radical scavengers such as α-tocopherol or esters thereof, superoxide dismutases or the like, certain metal chelating agents or ascorbic acid and esters thereof;

anti-seborrhoeic agents such as certain sulfur-containing amino acids, 13-cis-retinoic acid, cyproterone acetate;

other agents for combating the desquamative conditions of the scalp such as selenium disulfide, climbazole, undecylenic acid, ketoconazole, piroctone olamine (octopirox) or ciclopiroctone (ciclopirox);

in particular, they may be active agents that stimulate the regrowth and/or that promote the slowing down of hair loss, and more particularly exemplary are:

nicotinic acid esters, especially including tocopheryl nicotinate, benzyl nicotinate and $C_1$-$C_6$ alkyl nicotinates such as methyl or hexyl nicotinates;

pyrimidine derivatives, such as 2,4-diamino-6-piperidinopyrimidine 3-oxide or "Minoxidil" described in U.S. Pat. Nos. 4,139,619 and 4,596,812; Aminexil or 2,4-diaminopyrimidine 3-oxide described in WO 96/09048;

lipoxygenase-inhibiting agents or cyclooxidase-inducing agents that promote hair regrowth such as those described by the assignee hereof in EP-0,648,488;

anti-bacterial agents such as macrolides, pyranosides and tetracyclines, and especially erythromycin;

calcium antagonists, such as cinnarizine, nimodipine and nifedipine;

hormones, such as oestriol or the like, or thyroxine and salts thereof;

anti-androgens, such as oxendolone, spironolactone, diethylstilbestrol and flutamide;

steroid or non-steroid inhibitors of 5-α-reductases, such as those described by the assignee hereof in EP-0,964,852 and EP-1,068,858, or else finasteride;

ATP-dependent potassium channel agonists such as cromakalim and nicorandil; and plant extracts with propigmenting activity, such as chrysanthemum extracts as described in FR-2768343 and *Sanguisorba* extracts described in FR-2782920.

Preferably, the compound selected from ellagic acid, its salts, its metal complexes, its monoether or polyether, monoacylated or polyacylated derivatives and its carbonate or carbamate derivatives deriving from hydroxyl groups is combined with at least one other hair active agent selected from agents for combating the desquamative conditions of the scalp, agents that slow down hair loss or that promote its regrowth, and plant extracts with propigmenting activity.

The present invention also features administration of ellagic acid, its salts, its metal complexes, its monoether or polyether, monoacylated or polyacylated derivatives and its carbonate or carbamate derivatives deriving from hydroxyl groups, for treating canities.

This invention also features a regime or regimen for the cosmetic treatment of canities, wherein a composition as defined previously comprising at least one compound selected from ellagic acid, its salts, its metal complexes, its monoether or polyether, monoacylated or polyacylated derivatives and its carbonate or carbamate derivatives deriving from hydroxyl groups is administered or is applied to the area to be treated.

The present invention also features a cosmetic treatment regime or regimen useful to maintain the natural pigmentation of grey or white head hair and/or body hair, wherein a composition as defined previously comprising at least one compound selected from ellagic acid, its salts, its metal complexes, its monoether or polyether, monoacylated or polyacylated derivatives and its carbonate or carbamate derivatives deriving from hydroxyl groups is administered or is applied to the area to be treated.

The methods for treating canities and for pigmentation of grey or white head hair and/or body hair may also entail ingesting a composition comprising at least one compound selected from ellagic acid, its salts, its metal complexes, its monoether or polyether, monoacylated or polyacylated derivatives and its carbonate or carbamate derivatives deriving from hydroxyl groups.

The areas to be treated may be, for example and non-limitingly, the scalp, eyebrows, moustache and/or beard and any area of the skin covered with hair.

More particularly, the methods for the cosmetic treatment of canities and the natural pigmentation of grey or white head hair and/or body hair entail applying a composition that comprises at least one compound selected from ellagic acid, its salts, its metal complexes, its monoether or polyether, monoacylated or polyacylated derivatives and its carbonate or carbamate derivatives deriving from hydroxyl groups.

The cosmetic treatment methods for combating canities and/or for maintaining the natural pigmentation of grey or white head hair and/or body hair may, for example, entail applying the composition to the hair and scalp in the evening, keeping the composition on overnight and optionally shampooing in the morning, or washing the hair using this composition and again leaving it in contact for a few minutes before rinsing. The compositions according to the invention have proved particularly advantageous when they are applied in the form of an optionally rinse-out hair lotion or even in the form of a shampoo.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Demonstration of the Protection of Melanocytes by Ellagic Acid

1-A-1. Protocol for measuring the reactive oxygen species (ROS) generated by an $H_2O_2$ stress in cultured normal human melanocytes (NHMs)

The normal human melanocytes (NHMs) were inoculated at D0 at the density of $4 \times 10^4$ cells/cm$^2$. At D1, the culture medium was replaced with the 10 µM solution of 6-carboxy-2',7'-dichlorodihydrofluorescein diacetate, di[acetoxymethyl ester] in PBS ($H_2$DCFDA, C2938, Molecular Probes). After 20 min the $H_2$DCFDA solution was replaced with the culture medium. The NHMs were left for 30 min before adding the $H_2O_2$ solution (250 µM). The fluorescence was measured after 15 min in a fluoroscan (excitation: 485 nm, emission: 538 nm).

The compounds studied were used depending on their properties (concentration, preincubation time). N-Acetylcysteine (A9165, Sigma) was used as a reference molecule. The melanocytes were pretreated, 12 h/18 h at 37° C., with the compound studied in the culture medium, before being brought into contact for 20 minutes with $H_2$DCFDA (10 µM in PBS). The $H_2$DCFDA solution was then replaced with the culture medium containing the active agent studied. After incubating for 30 min, the oxidative stress was induced by addition of 250 µM of $H_2O_2$ to the culture medium. The fluorescence was measured after 15 min in a fluoroscan (excitation: 485 nm, emission: 538 nm).

1-A-2. Results:

The results represent the crude fluorescence data, from which the autofluorescence values of "blank" cells, expressed in fluorescence units (fu), obtained during a representative experiment, have been deducted.

The results are given in FIG. 1. A decrease of the reactive oxygen species is indeed observed in the presence of ellagic acid.

1-B-1. Protocol for measuring the viability (toxicity control):

The normal human melanocytes (NHMs) were inoculated at D0 at the density of $4 \times 10^4$ cells/cm$^2$. After adhesion of the cells (3 h), the compound studied was added to the culture medium. After 24 h to 48 h, the cell viability was measuring using Alamar Blue (UP669413 UPTIMA, Interchim) according to the instructions of the supplier.

Figure 2:
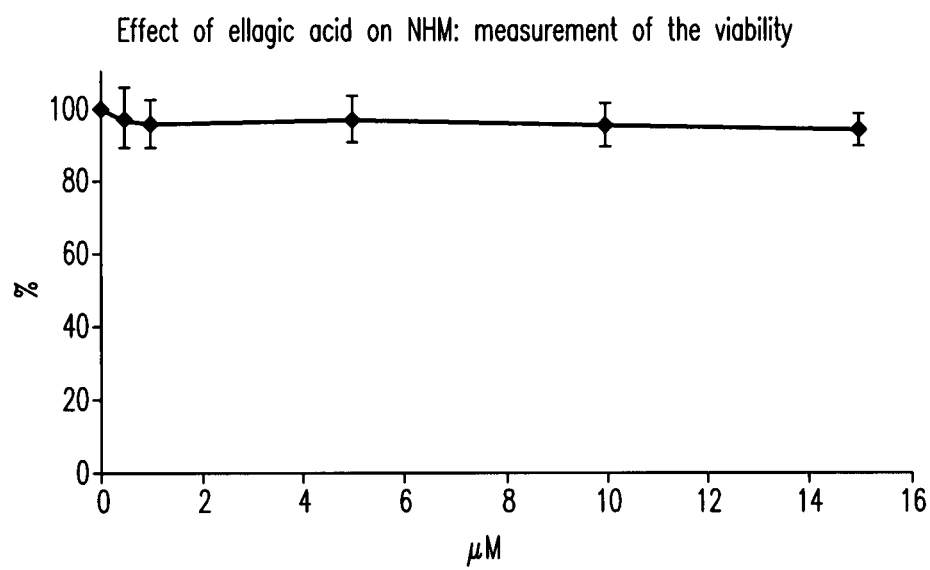
FIG. 2 is a graph showing the effect of ellagic acid on NHM: measurement of the viability.

1-B-2. Results:

The results represent the fluorescent signal percentages obtained for a representative experiment (measurement in triplicate) (2 independent experiments were carried out) and presented in the form of a % fluorescence curve as a function of the concentration of the active agent studied (in µM). The results are given in FIG. 2.

1-C-1. Protocol for accelerated senescence induced in vitro by a chronic $H_2O_2$ stress:

(According to O. Toussaint, E. E. Medrano and T. von Zglinicki, Experimental Gerontology 2000, 35, 927-945).

The normal human melanocytes (NHMs) were inoculated at D0 at the density of $0.8 \times 10^4$ cells/cm$^2$. After adhesion of the cells (3 h) the active agent studied was added to the culture medium. $H_2O_2$ (250 µM) was added to the culture medium over 1 hour, at D1, D2 and D3. In addition, the culture medium was renewed every two days without addition of stress. On D7, the number of viable cells was measured using Alamar Blue (UP669413 UPTIMA, Interchim) according to the instructions of the supplier.

1-C-2. Results:

The results illustrate the effect of ellagic acid (EA) on the accelerated senescence induced in vitro by a chronic $H_2O_2$ stress and show a significant increase in viability in the presence of ellagic acid.

The test was also carried out with N-acetylcysteine, which is a reference compound.

Figure 3:
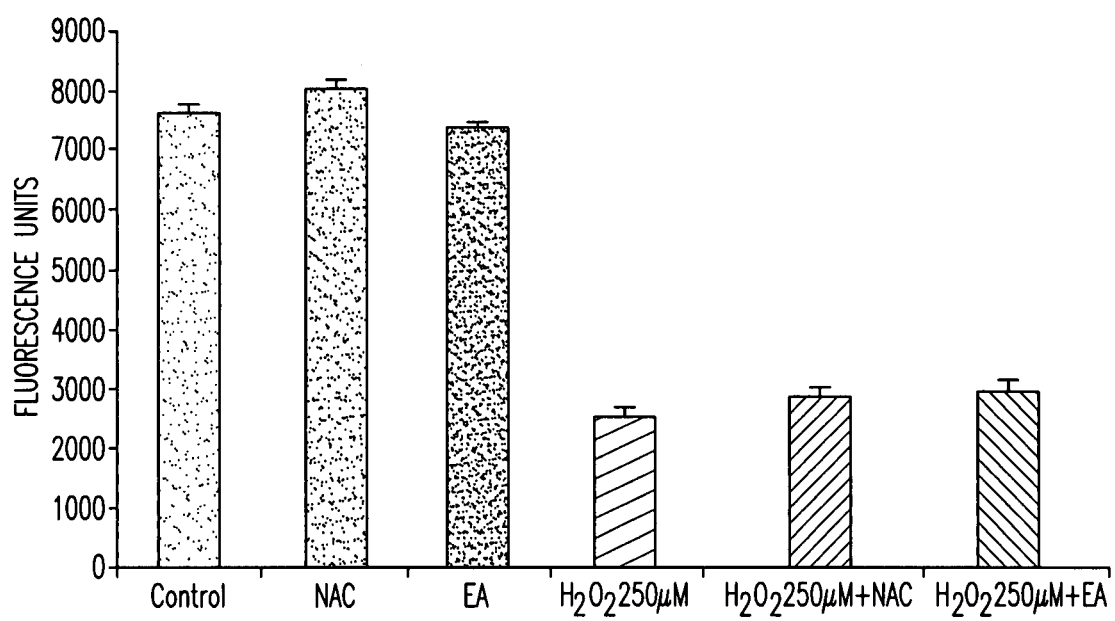
FIG. 3 is a graph showing the effect of ellagic acid: viability after induction of accelerated senescence by a chronic in vitro $H_2O_2$ stress.

The results are given in the table below and in FIG. 3.

|  | Control | NAC | EA | no treatment | NAC | EA |
|---|---|---|---|---|---|---|
| average fluorescence | 7601.67 | 8056.00 | 7343.67 | 2524.33 | 2869.00 | 2934.00 |
| standard deviation | 164.08 | 166.01 | 97.45 | 158.00 | 128.19 | 200.53 |
| % relative to the control | 100 | 106 | 97 | 33 | 38 | 39 |

Example 2

Compositions

Hair Lotion:

| ellagic acid | 0.5 g |
|---|---|
| propylene glycol | 20 g |
| 95° ethanol | 30 g |
| water | qs for 100 g |

This lotion was applied daily to the areas to be treated and preferably to the entirety of the scalp for at least 10 days and preferentially for 1 to 2 months.

A reduction in the appearance of white or grey hair and a repigmentation of grey hair was then observed.

Treating Shampoo:

| ellagic acid | 1.5 g |
|---|---|
| polyglyceryl-3 hydroxy aryl ether | 26 g |
| hydroxypropylcellulose marketed under the trademark KLUCELL G by Hercules | 2 g |
| preservatives | qs |
| 95° ethanol | 50 g |
| water | qs for 100 g |

This shampoo was used on each wash with an exposure time of around one minute.

A prolonged use, of around two months, resulted in the slowing down of canities and to the gradual repigmentation of grey hair.

This shampoo may also be used preventatively in order to delay hair whitening.

Treating Gel:

| ellagic acid | 0.75 g |
|---|---|
| essential *eucalyptus* oils | 1 g |
| econazole | 0.2 g |
| lauryl polyglyceryl-6 cetearyl glycol ether | 1.9 g |
| preservatives | qs |
| CARBOPOL 934P marketed by BF Goodrich Corporation | 0.3 g |
| neutralizing agent | qs pH 7 |
| water | qs for 100 g |

This gel was applied to the areas to be treated twice a day (morning and evening) with a final massage. After applying for three months, a repigmentation of the body hair or head hair in the area treated was observed.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for limiting development of canities comprising administering to a subject seeking to treat canities a composition comprising a thus effective amount of at least one compound selected from the group consisting of ellagic acid, its salts, its metal complexes, its monoether or polyether, monoacylated or polyacylated derivatives and its carbonate or carbamate derivatives deriving from hydroxyl groups, wherein said composition is administered orally for the purpose of limiting the development of canities, and wherein the compound is present in an amount from 0.001% to 10% by weight relative to the total weight of the composition.

2. A method for maintaining natural pigmentation of grey head hair and/or body hair comprising administering to a subject seeking to maintain natural pigmentation a composition comprising a thus effective amount of at least one compound selected from the group consisting of ellagic acid, its salts, its metal complexes, its monoether or polyether, monoacylated or polyacylated derivatives and its carbonate or carbamate derivatives deriving from hydroxyl groups, wherein said composition is administered orally to said subject for the purpose of maintaining natural pigmentation of grey head hair and/or body hair, and wherein the compound is present in an amount from 0.001% to 10% by weight relative to the total weight of the composition.

3. The method as defined by claim 1, said at least one compound being encapsulated in a coating of microspheres, nanospheres, oleosomes or nanocapsules.

4. The method of claim 1, wherein the compound is an amount from 0.01% to 5% by weight relative to the total weight of the composition.

5. The method of claim 1, wherein the compound is an amount from 0.1% to 1% by weight relative to the total weight of the composition.

6. The method of claim 1, wherein the composition is a dietary liquid.

7. The method of claim 6, wherein the dietary liquid is an optionally flavored aqueous solution or an optionally flavored aqueous-alcoholic solution.

8. The method of claim 1, wherein the composition is administered in the form of granules, pills, tablets, or sugar-coated tablets.

9. The method of claim 1, wherein the compound is ellagic acid.

10. The method of claim 2, wherein the compound is ellagic acid.

* * * * *